United States Patent
Ng

(10) Patent No.: US 12,280,139 B2
(45) Date of Patent: Apr. 22, 2025

(54) MICROPARTICLES/MICROCROWN

(71) Applicant: Grand Advance Technologies Pte Ltd, Singapore (SG)

(72) Inventor: Lee Huat Ng, Singapore (SG)

(73) Assignee: Grand Advance Technologies Pte Ltd, Singapore (SG)

( * ) Notice: Subject to any disclaimer, the term of this patent is extended or adjusted under 35 U.S.C. 154(b) by 0 days.

(21) Appl. No.: 17/738,407

(22) Filed: May 6, 2022

(65) Prior Publication Data

US 2022/0354780 A1  Nov. 10, 2022

(30) Foreign Application Priority Data

May 7, 2021 (SG) .............................. 10202104811R

(51) Int. Cl.
| | |
|---|---|
| B29C 33/48 | (2006.01) |
| A61K 9/00 | (2006.01) |
| B28B 3/26 | (2006.01) |
| B29C 48/03 | (2019.01) |
| B29B 9/12 | (2006.01) |

(52) U.S. Cl.
CPC .............. *A61K 9/0012* (2013.01); *B28B 3/26* (2013.01); *B29C 33/48* (2013.01); *B29C 48/131* (2019.02); *B29B 2009/125* (2013.01)

(58) Field of Classification Search
CPC ......... B29C 48/131; B29C 33/48; B28B 3/26; B29B 2009/125
USPC .......................................... 264/322, 334–335
See application file for complete search history.

(56) References Cited

U.S. PATENT DOCUMENTS

| | | | |
|---|---|---|---|
| 7,799,249 B2 * | 9/2010 | Goodenough | B29D 11/0048 264/2.6 |
| 2001/0020151 A1 | 9/2001 | Reed et al. | |
| 2003/0062640 A1 * | 4/2003 | Ansell | B29D 11/00125 264/1.32 |

FOREIGN PATENT DOCUMENTS

| | | |
|---|---|---|
| CN | 203293346 U | 11/2013 |
| GB | 2503651 A | 1/2014 |
| WO | 2014/167495 A1 | 10/2014 |
| WO | 2018/160140 A1 | 9/2018 |

OTHER PUBLICATIONS

Search Report with Written Opinion issued by the Intellectual Property Office of Singapore for Singapore Patent Application No. 10202104811R, mailed on Jun. 6, 2023.

(Continued)

*Primary Examiner* — Jeffrey M Wollschlager
*Assistant Examiner* — Xue H Liu
(74) *Attorney, Agent, or Firm* — JCIP; Joseph G. Chu

(57) ABSTRACT

A method of producing a microparticle includes providing a mould assembly, which comprises two moulds that comprise an upper mould and a lower mould, positioning the mould assembly in a closed position, wherein the two moulds define a micro-cavity to exert pressure on a moulding material within the micro-cavity to form the moulding material into a microparticle, and positioning the mould assembly in an open position, wherein the microparticle adheres to one of the two moulds of the mould assembly.

20 Claims, 2 Drawing Sheets

(56) References Cited

OTHER PUBLICATIONS

Figure 1:
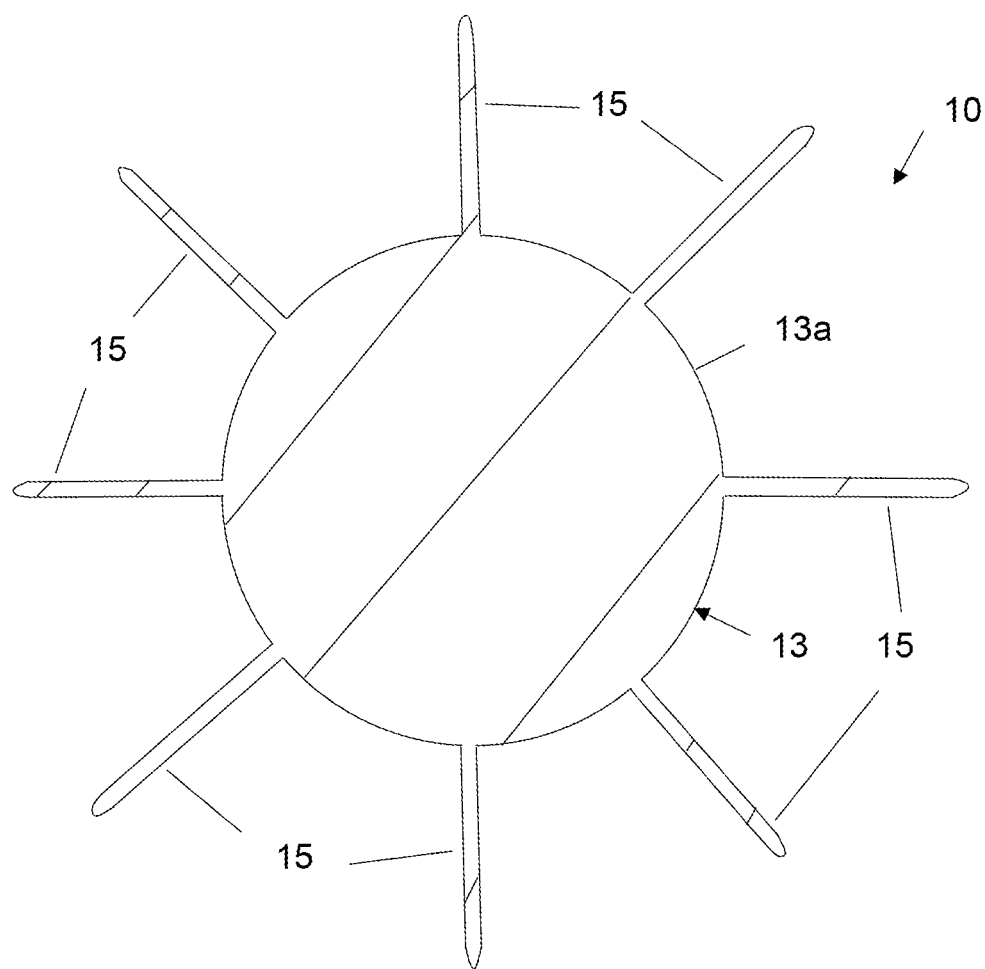

Lu et al., "Engineered PLGA microparticles for long-term, pulsatile release of STING agonist for cancer immunotherapy", Science Translational Medicine, Aug. 2020, vol. 12, No. 556.
Larraneta, et al., "Microneedle arrays as transdermal and intradermal drug delivery systems: Materials science, manufacture and commercial development", Materials Science and Engineering: R Reports, Apr. 2016, pp. 1-32, vol. 104.

* cited by examiner

MICROPARTICLES/MICROCROWN

This application claims priority under 35 U.S.C. § 119 to Singaporean Patent Application No. 10202104811R, filed on May 7, 2021, the contents of which are incorporated herein by reference in their entirety.

The application relates to microparticles.

The microparticles generally are particles with a size of between about 1 and about 1000 micron. The microparticles can be produced with a wide variety of materials, including ceramics, glass, polymers, and metals.

US20010020151A1 shows an apparatus for treating a patient. The apparatus includes a deployment mechanism. The apparatus includes at least one probe disposed on a surface of the deployment mechanism. The probe extends between 25 microns and 1000 microns from the surface of the deployment mechanism. The apparatus also includes material coated on the probe.

The patent also provides a method of treating a patient. The method includes a step of placing a material with a probe that extends less than 1000 microns from a surface of a deployment mechanism. Next, a step of inserting the probe into, preferably a blood vessel of a patient is performed. Then, a step of penetrating the interior wall of the vessel from the interior of the vessel with the probe is done by activating the deployment mechanism so the material can contact the vessel.

It is an objective of the application to provide an improved microparticle.

The application provides an improved method of producing a microparticle.

The microparticle serves as a micro crown. The micro crown can transport a medical substance through the skin. The microparticle often have several spikes. These spikes have a length that is long enough for transdermal delivery of a therapeutic or a cosmetic agent to a region inside or below a skin while being sufficiently short for avoiding contacting nerves in the skin to reduce the chances of bleeding and pain.

The therapeutic agent can include a drug for treating an illness while the cosmetic agent can include one or more essential oils or essence that are extracted from plants to prevent a disease from occurring or spreading.

The method includes a step of providing a mould assembly, which comprises two moulds. The moulds comprise an upper mould and a lower mould.

The mould assembly is then positioned in a closed position, wherein the two moulds define a micro-cavity to exert pressure on a moulding material within the micro-cavity to form the moulding material into a microparticle. The micro-cavity is also called cavity.

The mould assembly is later positioned in an open position, wherein the microparticle adheres to one of the two moulds of the mould assembly. This allows the microparticle to removed easily from the mould assembly.

The method provides a simple way for producing a microparticle.

The moulding material is often provided inside the mould assembly when the mould assembly is in an open position, although it can also be provided when the mould assembly is in a closed position.

Heat can be applied to the moulding material for softening the moulding material.

The microparticle is often removed from the mould assembly using a vacuum device.

The application also provides a further improved method of producing a microparticle.

The method comprises using pressure to inject a moulding material into a micro-cavity of a mould assembly, that is placed is a closed position. The moulding material then flows via a channel of the mould into the micro-cavity.

After this, the mould assembly is positioned in an open position, wherein the microparticle adheres to one of the two moulds of the mould assembly.

Heat can be applied to the moulding material for softening the moulding material.

The microparticle is often removed from the mould assembly using a vacuum device.

The application also provides another improved method of producing a microparticle.

The method includes a step of providing a die. The die includes an orifice with a cross-sectional profile that is essentially the same as a cross-sectional profile of the microparticle.

After this, the moulding material and the die are also pressed toward each other such that the moulding material passes through the orifice.

The moulding material that passes through the orifice has a cross-sectional profile that is essentially the same as the cross-sectional profile of the microparticle.

The moulding material that passes through the orifice is then cut such that the material that is cut forms a microparticle. The microparticle has spikes that extend in a two-dimensional plane.

The method provides a simple means of producing a microparticle.

The application also provides a microparticle that is produced with the above-described method.

The microparticle includes a body with a plurality of spikes. The body has a shape essentially of a sphere. The spikes extend from an outer surface of the body.

Each spike comprises a rod portion and an end portion. A first end of the rod portion is attached to the end portion and a second end of the rod portion is attached to the outer surface of the body. A longitudinal cross-section of the rod portion has a general shape of a trapezium.

In one embodiment, the diameter of the sphere is about 0.3 millimetre (mm), the length of the spike is about 0.1 mm, and the general diameter of the spike is about 0.03 mm.

An axis of the rod portion often extends about perpendicularly to the outer surface of the body.

The spikes are often distributed evenly across the outer surface.

The application provides a device for producing a microparticle. The device includes a first mould with a first inner surface and a second mould with a second inner surface.

The first mould and the second mould are adapted such that, in a closed position, the first inner surface of the first mould and the second inner surface of the second mould define a micro-cavity. A shape of the micro-cavity corresponds generally to a shape of the microparticle.

Also, the first mould and the second mould are adapted such that, in an open position, one of the first inner surface of the first mould and the second inner surface of the second mould adheres to the moulded microparticle while the other separates easily from the moulded microparticle.

The device provides a simple means for producing microparticles with low cost.

The application provides another improved device for producing a microparticle.

The device includes a first mould with a first inner surface, a second mould with a second inner surface, and a channel.

The first mould and the second mould are adapted such that, in a closed position, the first inner surface of the first mould and the second inner surface of the second mould define a micro-cavity. A shape of the micro-cavity corresponds generally to a shape of the moulded microparticle.

The channel includes an inlet for receiving a moulding material and an outlet for transferring the moulding material to the micro-cavity.

The first mould and the second mould are further adapted such that, in an open position, one of the first inner surface of the first mould and the second inner surface of the second mould adheres to the moulded microparticle while the other separates easily from the moulded microparticle.

The device provides another means for producing microparticles with low cost.

The first mould and the second mould are often produced by milling or cutting a block of material with a curved cutting surface of a first cutting tool to produce a body surface. A shape of the body surface corresponds generally to a shape of a body of the microparticle.

The block of material is then milled with a partial cone cutting surface of a second cutting tool to produce a rod surface. A shape of the rod surface corresponds generally to a surface of a rod surface of a spike of the microparticle.

After this, the block of material is milled with a curved cutting surface of a third cutting tool to produce an end portion rod surface. A shape of the end portion corresponds generally to an end portion of the spike of the microparticle.

The application also provides another improved device for producing a microparticle.

The device includes a die, a pressing device, and a cutting device.

In particular, the die includes an orifice or opening with a profile that is essentially the same as a profile of the microparticle. The die is also called a mould.

The pressing device is used for pressing a moulding material and the die toward each other.

The cutting device is used for cutting the moulding material that comes out or emerges out of the orifice, wherein the cut material forms a microparticle. Spikes of the microparticle extend in a two-dimensional plane.

This device provides another means for producing a microparticle quickly with low cost.

Figure 2:
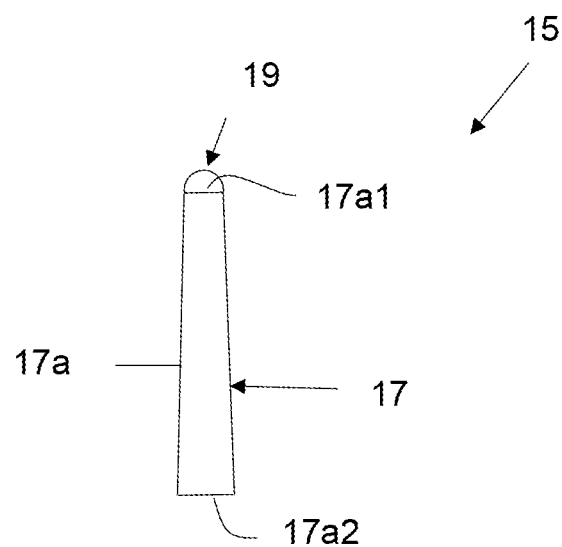
Figure 3:
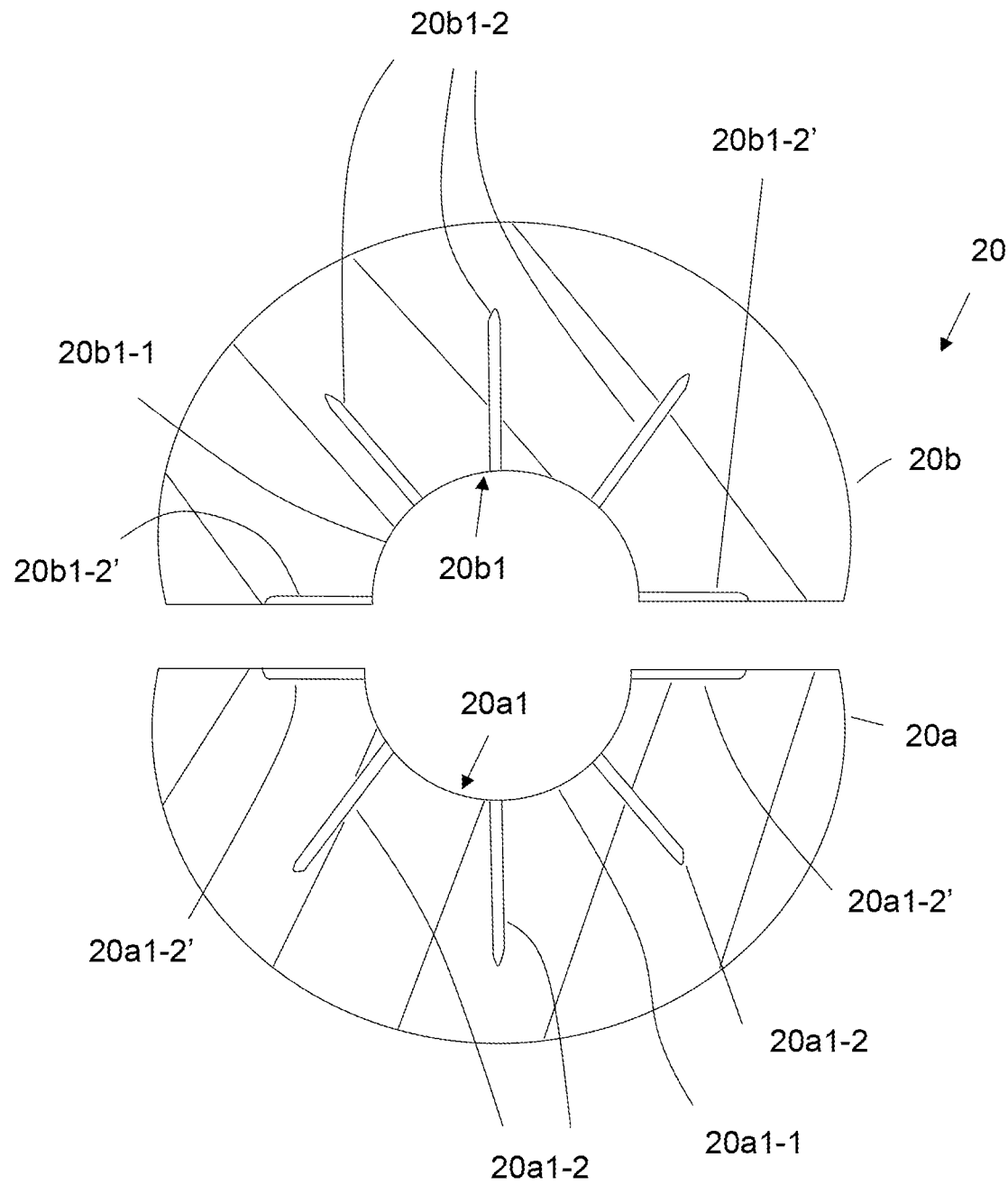

The subject matter of the application is described in greater detail in the accompanying Figures, in which, FIG. 1 illustrates a cross-sectional view of a microparticle, FIG. 2 illustrates a front view of a spike of the microparticle of FIG. 1, FIG. 3 illustrates a cross-sectional view of a mould assembly to produce the microparticle of FIG. 1.

In the following description, details are provided to describe the embodiments of the specification. It shall be apparent to one skilled in the art, however, that the embodiments may be practised without such details.

Some parts of the embodiments have similar parts. The similar parts may have the same names or similar component numbers with an alphabet symbol or prime symbol. The description of one part applies by reference to another similar part, where appropriate, thereby reducing repetition of text without limiting the disclosure.

FIG. 1 shows a microparticle 10 that includes a microparticle body 13 and a plurality of spikes 15. The microparticle 10 is also called a microsphere. The spikes 15 extend from an outer surface 13a of the body 13, and they are distributed essentially evenly across the outer surface 13a.

The microparticle body 13 has a shape mostly of a sphere.

As seen in FIG. 2, each spike 15 includes a rod portion 17 and an end portion 19. One end of the rod portion 17 is integrally attached to the end portion 19 while another end of the rod portion 17 is integrally attached to the outer surface 13a of the microparticle body 13, as illustrated in FIG. 1.

The end portion 19 includes a curved outer surface 19a. The curved outer surface 19a can have a shape of a partial sphere.

The rod portion 17 includes a partial cone body 17a. The partial cone body 17a is without a vertex portion and it includes a small flat end surface 17a1 with a circular edge and a large flat end surface 17a2 with another circular edge. The large flat end surface 17a2 is called a base while the small flat end surface 17a1 is called a top surface. The top surface 17a1 is placed facing the base 17a2.

The longitudinal cross-section of the partial cone body 17a has a shape of a trapezium. The trapezium has 4 straight sides of which one pair of opposite sides is parallel.

The top surface 17a1 of the rod portion 17 is integrally attached to the end portion 19. In contrast, the base 17a2 of the rod portion 17 is integrally attached to the outer surface 13a of the microparticle body 13. This attachment is done such that an axis of the partial cone body 17a extends about perpendicularly to the outer surface 13a of the microparticle body 13.

The spikes 15 have substantially the same length, although, in a general sense, they also can have different lengths.

The diameter of the microparticle body 13 is about 0.3 millimetre (mm), the length of the spike 15 is about 0.1 mm, and the general diameter of the spike 15 is about 0.03 mm.

In a general sense, the microparticle body 13 can also have other dimensions.

The microparticle 10 can be made by one or more members of a group consisting of gelatine, gelatine methacrylate hydrogel, hyaluronic acid, silicone, polymer, sugar, glass, ceramic and metal.

In use, the microparticle 10 acts as a micro crown, wherein the microparticle 10 has several spikes. These spikes have a length that is long enough for transdermal delivery of a therapeutic or a cosmetic agent to a region inside or below a skin while being sufficiently short for avoiding contacting nerves in the skin to reduce the chances of bleeding and pain. In short, the microparticle 10 transports a medical substance through the skin.

The therapeutic agent includes a drug for treating an illness. On the other hand, the cosmetic agent comprises one or more essential oils or essence that are extracted from plants to prevent a disease from occurring or spreading.

In one example, the body and the spikes of microparticle 10 are produced from a substance that includes a therapeutic or a cosmetic agent. In another example, the body and spikes are coated with a therapeutic or a cosmetic agent. In a further example, the body of the microparticle 10 encapsulates a therapeutic or a cosmetic agent. In short, the body has a solid part that comprises the therapeutic or the cosmetic agent. The microparticle 10 works as a carrier to carry with substances containing the therapeutic or the cosmetic agent.

Several other ways of using the microparticle 10 are possible.

The microparticles 10 can be included in a substance for inhaling to treat diseases, such as COVID-19.

The microparticles 10 can also be used to coat a surface of an object such that the surface is easy to clean.

The microparticles 10 can also be part of paint for sealing gaps, for producing a fragrance, or for killing germs.

In another embodiment, the microparticles 10 are a part of a skincare product to make the skin more beautiful.

In one case, a case encapsulates the microparticles 10 for oral delivery of drugs to a patient.

In a further embodiment, a derma roller includes a plurality of microcrowns. Each microcrown comprises a microparticle 10. In use, a user places the derma roller on the skin of a patient. The user then presses the derma roller against the skin and rolls the derma roller across the skin, wherein the microcrowns penetrate a thin surface of the skin for treating the skin.

FIG. 3 shows a mould assembly 20 to produce the microparticle 10.

The mould assembly 20 includes a stationary mould 20a and a moveable mould 20b. The mould 20a or 20b is also called a die.

The stationary mould 20a is attached to a machine bed. The machine bed refers to a fixed supporting surface, which is not illustrated in FIG. 3. The moveable mould 20b is positioned next to the stationary mould 20a.

The stationary mould 20a includes an inner surface 20a1 while the moveable mould 20b includes an inner surface 20b1. In a closed position, the internal surfaces 20a1 and 20b1 define an internal microcavity. The microcavity for simplicity is also called a cavity in this description. The shape of the microcavity corresponds to the shape of the microparticle 10.

Referring to the stationary mould 20a, the inner surface 20a1 includes a mould-body surface 20a1-1 and several mould-spike surfaces 20a1-2 with several partial mould-spike surfaces 20a1-2'. The mould-body surface 20a1-1 is connected to the mould-spike surfaces 20a1-2 and to the partial mould-spike surfaces 20a1-2'.

Similarly, the moveable mould 20b, the inner surface 20b1 includes a mould-body surface 20b1-1 and several mould-spike surfaces 20b1-2 with several partial mould-spike surfaces 20b1-2'. The mould-body surface 20b1-1 is connected to the mould-spike surfaces 20b1-2 and to the partial mould-spike surfaces 20b1-2'.

The shape of the mould-body surface 20a1-1 together with the mould-body surface 20b1-1 correspond to the shape of the body 13 of the microparticle 10.

The shape of the mould-spike surface 20a1-2 corresponds to the shape of the spike 15 of the microparticle 10. Likewise, the shape of the mould-spike surface 20b1-2 corresponds to the shape of the spike 15 of the microparticle 10.

The partial mould-spike surface 20a1-2' together with the respectively partial mould-spike surface 20b1-2' correspond to the shape of the spike 15 of the microparticle 10.

The mould-spike surface 20a1-2 includes a mould-rod surface and a mould end-portion surface. The mould-rod surface corresponds to the surface of the rod portion 17. The mould end-portion surface corresponds to the end portion 19.

Similarly, the mould-spike surface 20b1-2 includes a mould-rod surface and a mould end-portion surface. The mould-rod surface corresponds to the surface of the rod portion 17. The mould end-portion surface corresponds to the end portion 19.

A method of producing the mould assembly 20 is described below.

The method includes a step of providing a block of material for producing the stationary mould 20a.

A user then uses a first cutter tool with a curved cutting surface for milling or cutting a surface of the block of material to produce or create the mould-body surface 20a1-1 of a stationary mould 20a. The first cutter tool is also called a bead end mill.

After this, the user uses a second cutter tool with a partial cone cutting surface for milling the mould-body surface 20a1-1 to create several mould-rod surfaces on the mould-body surface 20a1-1.

The user later uses a third cutter tool with a curved cutting surface for milling or cutting each mould-rod surface to create a mould end-portion surface on each mould-rod surface.

Steps, which are similar to the above steps for producing the stationary mould 20a, are later applied to produce the moveable mould 20b.

In one implementation, about 2 to 3 hours of programming and more than 100 machine hours are taken to produce a mould assembly 20, as described above.

Operationally, the mould assembly 20 is moveable between an open position and a closed position.

In the open position, the moveable mould 20b is positioned apart or away from the stationary mould 20a for receiving a moulding substance or moulding material.

In contrast, in the closed position, the stationary mould 20a is positioned next to the moveable mould 20b such that the stationary mould 20a and the moveable mould 20b define the internal mould cavity. The closed position is used to press the moulding substance such that the moulding substance takes up the shape of the internal mould cavity to form into the desired microparticle.

A method of producing the microparticle 10 using compression moulding is described below.

The method includes a step to provide a mould assembly 20 with a first mould and a second mould.

The first mould is dimensioned such that it sticks to a moulded microparticle. In contrast, the second mould is dimensioned such that it does not hold or stick to the moulded microparticle.

In one example, the first mould refers to the stationary mould 20a while the second mould refers to the moveable mould 20b. In another example, the first mould refers to the moveable mould 20b while the second mould refers to the stationary mould 20a.

Heat is then applied to a suitable pliable moulding material for softening the moulding material.

The mould assembly 20 is then placed in an open position, wherein the first and the second moulds are separated from each other.

The moulding material is later inserted in the mould assembly 20.

After this, the mould assembly 20 is later placed in a closed position, wherein the first mould and the second press against each other to define an internal cavity.

This pressing also compresses the moulding material, wherein the moulding material takes up the shape of the internal cavity such that the moulding material forms into the desired microparticle.

The moulding material later solidifies when it is cooled sufficiently.

Subsequently, the mould assembly 20 is placed in the open position, wherein the moulded microparticle sticks to the first mould and not to the second mould of the mould assembly 20.

The solidified microparticle is afterwards removed from the micro-cavity of the mould assembly 20 using a vacuum device.

The sticking of the moulded microparticle to one mould and not to the other mould allows easy removal of the moulded microparticle.

Other methods of producing the microparticle 10 are also possible.

A method of producing a microparticle using injection moulding is described below.

The method includes a step to provide an injection mould assembly with a first mould and a second mould.

The first mould is dimensioned such that it sticks to a moulded microparticle while the second mould is dimensioned such that it does not hold or stick to the moulded microparticle.

The injection mould assembly is placed in a closed position, wherein the two moulds define a micro-cavity and a channel or runner. An outlet of each runner is connected to the micro-cavity.

Heat is applied to a suitable pliable moulding material to soften the moulding material.

A high-pressure device then injects the pliable moulding material into an inlet of the runner, wherein the moulding material flows to the outlet of the runner and into the micro-cavity.

The moulding material then takes up the shape of the micro-cavity and forms into a microparticle.

Subsequently, the mould assembly is placed in an open position, wherein the moulded microparticle sticks to the first mould and not to the second mould of the injection mould assembly.

The microparticle is later removed from the mould assembly using a vacuum device.

A method of producing a microparticle using micro-extrusion is described below.

The method includes a step of providing a die or mould for producing the microparticle. The die has an orifice. The shape or edge of the orifice is essentially the same as the profile or outline of the microparticle.

A suitable pliable moulding material is then pressed against the die, wherein the moulding material is squeezed through the orifice of the die such that the material that passes through the orifice has a profile that is essentially the same as the profile of the desired microparticle.

A cutting device then cuts this material that comes out of the die. The cut material forms a microparticle with spikes that extend in a two-dimensional plane.

In a special embodiment, instead of pressing the die against the pliable moulding material, the die is pressed against the moulding material.

This process can also be done at a high temperature for softening the moulding material.

Although the above description contains many specificities, these should not be construed as limiting the scope of the embodiments but merely providing an illustration of the foreseeable embodiments. Especially the above-stated advantages of the embodiments should not be construed as limiting the scope of the embodiments but merely to explain possible achievements if the described embodiments are put into practice. Thus, the scope of the embodiments should be determined by the claims and their equivalents, rather than by the examples that are given.

REFERENCE NUMBERS 10 microparticle
13 body
15 spike
13a outer surface
17 rod portion
17a partial cone body
17a1 small flat end surface
17a2 large flat end surface
19 end portion 19
19a curved outer surface
20 mould assembly
20a stationary mould
20a1 inner surface
20a1-1 mould-body surface
20a1-2 mould-spike surface
20a1-2' mould-spike surface
20b moveable mould
20b1 inner surface
20b1-1 mould-body surface
20b1-2 mould-spike surface
20b1-2' mould-spike surface

The invention claimed is:

1. A method of producing a microparticle, the method comprising:
    providing a mould assembly, which comprises two moulds that comprise a first mould and a second mould,
    positioning the mould assembly in an open position, wherein the first and second moulds are separated from each other,
    providing a pliable moulding material to the mould assembly in the open position,
    heating the pliable moulding material to soften the moulding material,
    positioning the mould assembly in a closed position to define a micro-cavity,
    pressing the first and second moulds against each other to cause the first and second moulds to press the softened pliable moulding material within the micro-cavity to take up the shape of the micro-cavity to form the softened pliable moulding material into a microparticle with a size of between about 1 and about 1000 micron, and
    positioning the mould assembly in the open position after the microparticle is moulded, wherein the microparticle adheres to one of the two moulds of the mould assembly,
    wherein one of the first and second moulds is dimensioned such that it sticks to the moulded microparticle and wherein the other of the first and second moulds is dimensioned such that it does not hold or stick to the moulded microparticle.

2. The method according to claim 1, further comprising:
    removing the microparticle from the mould assembly using a vacuum device.

3. The method according to claim 1, further comprising: cooling the moulding material to solidify the moulding material.

4. The method according to claim 1, wherein the first and second moulds are harder than the pliable material.

5. The method according to claim 1, wherein the first and second moulds are milled or cut moulds that are milled or cut from a block of material.

6. The method according to claim 1, wherein the first mould comprises an inner surface including a mould-body surface and several mould-spike surfaces with several partial mould-spike surfaces.

7. The method according to claim 6, wherein the second mould comprises an inner surface including a mould-body surface and several mould-spike surfaces with several partial mould-spike surfaces.

8. A device for producing a microparticle, the device comprising:
a first mould; and
a second mould,
wherein
the first mould and the second mould are adapted such that,
in a closed position, the first mould and the second mould define a micro-cavity and are pressed against each other to compress a pliable moulding material within the micro-cavity, wherein a shape of the micro-cavity corresponds to a shape of the microparticle, and
in an open position, one of the first mould and the second mould adheres to the microparticle while the other separates from the microparticle,
wherein one of the first and second moulds is dimensioned such that it sticks to the moulded microparticle and wherein the other of the first and second moulds is dimensioned such that it does not hold or stick to the moulded microparticle.

9. The device according to claim 8, wherein each of the first mould and the second mould is a milled or cut mould that is produced by milling a block of material with a curved cutting surface of a first cutting tool to produce a body surface, a shape of the body surface corresponds to a shape of a body of the microparticle.

10. The device according to claim 9, wherein the block of material is further milled with a partial cone cutting surface of a second cutting tool to produce a rod surface, a shape of the rod surface corresponds to a surface of a rod surface of a spike of the microparticle.

11. The device according to claim 10, wherein the block of material is further milled with a curved cutting surface of a third cutting tool to produce an end portion rod surface, a shape of the end portion corresponds to an end portion of the spike of the microparticle.

12. The device according to claim 8, wherein the first mould comprises an inner surface including a mould-body surface and several mould-spike surfaces with several partial mould-spike surfaces.

13. The device according to claim 12, wherein the second mould comprises an inner surface including a mould-body surface and several mould-spike surfaces with several partial mould-spike surfaces.

14. The device according to claim 13, wherein a shape of the mould-body surface of the first mould and a shape of the mould-body surface of the second mould correspond to the shape of the microparticle.

15. A method of producing a microparticle, the method comprising:

providing a mould assembly, which comprises two moulds that comprise a stationary mould and a moveable mould, wherein one or both of the stationary and moveable moulds comprises an inner surface including a mould-body surface and several mould-spike surfaces with several partial mould-spike surfaces, positioning the mould assembly in an open position, wherein the stationary and moveable moulds are separated from each other, providing a polymeric material to the mould assembly in the open position, wherein the polymeric material is more pliable than the mould assembly, positioning the mould assembly in a closed position to define a micro-cavity, pressing the moveable moulds against the stationary mould to cause the stationary and moveable moulds to compress the polymeric material within the micro-cavity to take up the shape of the micro-cavity to form the polymeric material into a microparticle, and positioning the mould assembly in the open position after the microparticle is moulded, wherein the microparticle adheres to one of the two moulds of the mould assembly, wherein one of the stationary and moveable moulds is dimensioned such that it sticks to the moulded microparticle and wherein the other of the stationary and moveable moulds is dimensioned such that it does not hold or stick to the moulded microparticle.

16. The method according to claim 15, wherein the stationary mould is attached to a fixed supporting surface.

17. The method according to claim 15, further comprising:
heating the polymeric material to soften the polymeric material.

18. The method according to claim 17, further comprising:
cooling the polymeric material to solidify the polymeric material after the polymeric material forms into the microparticle.

19. The method according to claim 15, further comprising:
removing the microparticle from the mould assembly using a vacuum device.

20. The method according to claim 15, where the moulded microparticle has a size of between about 1 to about 1000 micron.

* * * * *